(12) United States Patent
Cano

(10) Patent No.: US 6,168,604 B1
(45) Date of Patent: Jan. 2, 2001

(54) GUIDE WIRE DEVICE FOR REMOVING SOLID OBJECTS FROM BODY CANALS

(75) Inventor: Gerald G. Cano, Penn Hills, PA (US)

(73) Assignee: Metamorphic Surgical Devices, LLC, Pittsburgh, PA (US)

( * ) Notice: Under 35 U.S.C. 154(b), the term of this patent shall be extended for 0 days.

(21) Appl. No.: 09/400,336

(22) Filed: Sep. 21, 1999

Related U.S. Application Data

(63) Continuation-in-part of application No. 09/013,178, filed on Jan. 26, 1998, which is a continuation-in-part of application No. 08/539,875, filed on Oct. 6, 1995, now Pat. No. 5,779,716.

(51) Int. Cl.⁷ .................................................. A61B 17/22

(52) U.S. Cl. ...................... 606/114; 606/113; 606/127; 606/110

(58) Field of Search ..................... 606/114, 113, 606/110, 127, 108, 200, 194; 600/37

(56) References Cited

U.S. PATENT DOCUMENTS

| 2,856,933 | 10/1958 | Hildebrand et al. | 128/305 |
|---|---|---|---|
| 3,181,533 | 5/1965 | Heath | 128/320 |
| 3,952,747 | 4/1976 | Kimmell, Jr. | 128/303 R |
| 4,425,908 | 1/1984 | Simon | 128/1 R |
| 4,665,906 | 5/1987 | Jervis | 128/92 YN |
| 4,688,553 | 8/1987 | Metals | 128/1 R |
| 4,723,549 | 2/1988 | Wholey et al. | 128/344 |
| 4,727,873 | 3/1988 | Mobin-Uddin | 128/303 R |
| 4,873,978 | 10/1989 | Ginsburg | 128/345 |
| 5,067,957 | 11/1991 | Jervis | 606/108 |
| 5,098,440 * | 3/1992 | Hillstead | 606/108 |
| 5,147,371 | 9/1992 | Washington et al. | 606/127 |
| 5,188,111 | 2/1993 | Yates et al. | 128/657 |
| 5,190,542 | 3/1993 | Nakao et al. | 606/47 |
| 5,190,546 | 3/1993 | Jervis | 606/78 |
| 5,190,555 | 3/1993 | Wetter et al. | 606/114 |
| 5,192,284 | 3/1993 | Pleatman | 606/114 |
| 5,192,286 | 3/1993 | Phan et al. | 606/127 |
| 5,201,740 | 4/1993 | Nakao et al. | 606/113 |
| 5,201,741 | 4/1993 | Dulebohn | 606/113 |
| 5,215,521 | 6/1993 | Cochran | 604/22 |
| 5,234,439 | 8/1993 | Wilk et al. | 606/114 |
| 5,279,539 | 1/1994 | Bohan et al. | 600/37 |
| 5,312,416 | 5/1994 | Spaeth et al. | 606/114 |

(List continued on next page.)

FOREIGN PATENT DOCUMENTS 9833443    8/1998 (WO) .................. A61B 17/22

OTHER PUBLICATIONS

Fadali, A. Moneim, M.D. et al., entitled "A filtering device for the prevention of particulate embolization during the course of cardiac surgery", Surgery, Sep. 1968, vol. 62, No.3, pp. 634–639.

*Primary Examiner*—Pedro Philogene
(74) *Attorney, Agent, or Firm*—Webb Ziesenheim Logsdon Orkin & Hanson, P.C.

(57) ABSTRACT

A vascular filter for capturing and removing emboli includes a sack having a mouth and a closed bottom opposite the mouth. A guide wire is received through the mouth of the sack and projected through the closed bottom of the sack. The closed bottom of the sack is connected to the projection of the guide wire therethrough. A collapsible frame is connected between the guide wire and the mouth of the sack. The collapsible frame biases the mouth of the sack open around the guide wire. A tube slidably receives the guide wire coaxially therein. The collapsible frame is moveable via the guide wire between outside the tube where the mouth of the sack is biased open by the collapsible frame and inside the tube where the mouth of the sack is closed, and vice versa.

20 Claims, 4 Drawing Sheets

U.S. PATENT DOCUMENTS

| | | | |
|---|---|---|---|
| 5,312,417 | 5/1994 | Wilk | 606/114 |
| 5,341,815 | 8/1994 | Cofone et al. | 128/749 |
| 5,352,184 | 10/1994 | Goldberg et al. | 600/37 |
| 5,354,303 | 10/1994 | Spaeth et al. | 606/128 |
| 5,366,460 | 11/1994 | Eberbach | 606/151 |
| 5,368,597 | 11/1994 | Pagedas | 606/114 |
| 5,480,404 | 1/1996 | Kammerer et al. | 606/113 |
| 5,486,182 | 1/1996 | Nakao et al. | 606/114 |
| 5,486,183 | 1/1996 | Middleman et al. | 606/127 |
| 5,549,626 | 8/1996 | Miller et al. | 606/200 |
| 5,611,803 | 3/1997 | Heaven et al. | 606/114 |
| 5,669,933 | 9/1997 | Simon et al. | 600/200 |
| 5,695,519 * | 12/1997 | Summers et al. | 606/200 |
| 5,769,816 * | 6/1998 | Barbut et al. | 606/200 |
| 5,814,064 * | 9/1998 | Daniel et al. | 606/200 |
| 5,836,968 | 11/1998 | Simon et al. | 606/200 |
| 5,853,374 | 12/1998 | Hart et al. | 600/562 |

* cited by examiner

GUIDE WIRE DEVICE FOR REMOVING SOLID OBJECTS FROM BODY CANALS

CROSS REFERENCE TO RELATED APPLICATIONS

This application is a continuation-in-part of U.S. patent application Ser. No. 09/013,178 filed, Jan. 26, 1998 entitled "Device for Removing Solid Objects from Body Canals, Cavities and Organs Including an Invertible Basket" which is a continuation-in-part of U.S. patent application Ser. No. 08/539,875 filed Oct. 6, 1995 entitled "Device for Removing Solid Objects from Body Canals, Cavities and Organs", now U.S. Pat. No. 5,779,716 granted on Jul. 14, 1998.

BACKGROUND OF THE INVENTION

1. Field of the Invention

The present invention relates to a device for removing clot and embolic material from vessels of the cardiovascular system and, more particularly, to a device having a deployable sack attached to a guide wire adjacent a distal end of the guide wire.

2. Description of the Prior Art

Within body canals, specifically vessels of the cardiovascular system, capture and removal of thromboemboli is of significant clinical importance. Thrombus is an aggregation of platelets, fibrin, clotting factors and cellular components of blood that spontaneously form and attach on the interior wall of a vein or artery, partially or completely occluding the lumen.

Thrombus formation is either acute or chronic. Chronic formation can be related to a genetic propensity or a physiologic response to foreign material such as atrio-ventricular grafts in dialysis patients. Chronic formation causes the gradual reduction in the lumen of a vessel with a reduction of oxygen delivery to associated tissue. Treatment may involve balloon angioplasty, balloon angioplasty with stenting, thrombolysis, or thrombolysis with thrombectomy. Acute formation may be a response to blunt force trauma or an embolic event. Acute formation immediately causes complete occlusion of the lumen of a vessel. In peripheral vessels, treatment in response to acute formation may involve lysis with, for example, urokinase, embolectomy, or both.

Embolic events occur randomly during certain practiced and emerging clinical procedures for treatment of chronic situations. They are attributed to thrombus or plaque (cholesterol and cellular debris) that becomes mobile within the blood stream during a procedure, only to relocate to other smaller vessels to obstruct blood flow. Resulting complications include stroke, myocardial infarction, kidney failure, limb loss or even death. These complications can be reduced through use of a device to capture emboli inadvertently created during the procedure.

Embolectomy is a well-accepted procedure. It is a through lumen, device mediated procedure to mechanically remove clot formations from a vessel. A Fogarty balloon catheter is a commonly used device to perform an embolectomy. Embolectomy is the procedure of choice for the patient with an acute embolus in the peripheral vasculature. Immediate treatment is often required to salvage limbs. Causes of acute embolus include rheumatic heart disease, arteriosclerotic heart disease, atrial fibrillation and blunt force trauma.

The Fogarty balloon catheter is meant for acute cases. The vessel in which an embolus has lodged is identified and the position of the embolus within the vessel located. The lumen of the vessel is then accessed, either through a cut-down or though an access port. If a cut-down is used, the vessel is clamped to the side of the cut-down away from the clot. The Fogarty catheter is then inserted into the vessel lumen and the unexpanded balloon advanced past the clot. The balloon is then inflated and pulled toward the cut-down. As the balloon nears the cut-down, the clot is pushed out the cut-down.

Approximately 6% of patients undergoing Fogarty catheterization experience complications, specifically, retrograde balloon pullback injury leading to intimal hyperplasia and vessel restenosis. Simply sliding the balloon against the intima causes damage thereto—the higher the pressure, the more severe the damage. Thus, manufacturers caution about maximum pull force applied when using a Fogarty balloon catheter.

Since the Fogarty balloon catheter is a high pressure balloon, it cannot remove small clots, particularly when the vessel lining is irregular. In addition, losses of 10% to 20% of clots with the balloon are attributed to various causes.

For the acute patient, treatment with urokinase is controversial. It is a treatment of convenience for the physician, but confines a patient to an intensive care unit (ICU) for up to 72 hours, exposing the patient to dangers associated with clot migration, such as renal failure, myocardial infarction, hematoma and even death. Also of issue are treatment costs due to confinement to the ICU and a large amount of urokinase.

Distal protection during interventional and surgical procedures is a concept of growing importance to reduce the risk of embolic events. Devices to mediate the risk of embolic events are just being asked for to a larger degree by interventionalists. These devices act as an intervening filter downstream between the source of clot or plaque and a vulnerable site. Procedures that experience substantial risk from embolic events and the proposed means to manage the risk, include percutaneous transluminal coronary angioplasty (PTCA) with or without stent placement and saphenous vein graft maintenance (placement of protection in coronary vessels); carotid angioplasty with stent placement (placement of protection in the carotid); and coronary artery by-pass grafts and aortic aneurysm repair (placement of protection in the aorta).

Stenosis or occlusion of coronary vessels is common. Treatment is either coronary artery by-pass graft (CABG) surgery or percutaneous transluminal coronary angioplasty (PTCA). CABG surgery is a widely used surgical procedure to reestablish normal blood flow to cardiac muscle beyond a stenosis or occlusion in a coronary artery by grafting another vessel to the artery to shunt blood around the occlusion. The graft is harvested from another site, usually the leg, in the patient. The saphenous vein is most frequently used for the graft.

PTCA is a preferable alternative to CABG in the treatment of stenosis. In this guide wire/catheter-based procedure, a high-pressure balloon is positioned across the stenosis and inflated to deform the stenotic lesion to augment the effective lumen of the vessel and thus return adequate blood flow. The vessel may receive additional radial support by positioning and expanding a coronary stent across the lesion.

Clinical experience now indicates that, within five to ten years of CABG, however, a saphenous vein graft (SVG) can become diseased as the saphenous vein develops in the low pressure venous system and is not sufficiently robust for the high pressure arterial system. The disease is expressed as an accumulation of plaque or thrombus in the graft that again reduces perfusion of the cardiac muscle.

In performing carotid angioplasty with stent placement, strokes can result. Stroke is the death of neurons attributable to reduced oxygenation due to interrupted blood flow. Resultant damage frequently is permanent.

While stroke is often a random, unpredicted occurrence, it may also be a component of procedures of the carotid artery leading to the brain. It is not uncommon for the carotid artery to become clogged with plaque. Treatment, until recently, has been carotid endarterectomy, the surgical removal of the obstructive material. Complication rate is 3% to 6%, depending on whether the patient is symptomatic or asymptomatic.

Recently, stent-supported carotid angioplasty has emerged as a potential alternative. Unfortunately, emboli are a potential by-product of the procedure, placing the patient at risk to stroke. Exacerbating the risk is the brain's susceptibility to even small particles. While the incidence of stroke may be at an acceptable level for the highly skilled practitioner, the incidence of stroke is likely to increase as the procedure is performed by the average practitioner. Consequently, wide use of the procedure is dependent upon a reasonably transparent means to intercept even very minute particles of plaque dislodged during the procedure. A temporary carotid filter will significantly reduce the likelihood of stroke as carotid stenting increases.

Coronary artery by-pass grafts (CABGs) surgery, the standard open-chest procedure to restore adequate blood flow to the heart muscle, involves stopping the heart, clamping the aorta near its origin at the top of the left ventricle, placing the patient on external by-pass, locating the coronary artery or arteries that are blocked, harvesting the graft, completing the anastomosis, restarting the heart, unclamping the aorta and removing the patient from external by-pass.

Development of plaque is a multi-vessel disease. Presence in the coronary arteries portends build-up in the aorta. Particulate emboli have been recognized as occurring during cardiac surgery and release of particulate emboli during cardiac surgery has been linked to the release of the aortic clamp. Moreover, an increased risk of stroke in individuals with atherosclerotic disease of the ascending aorta and aortic arch have been reported. Furthermore, transesophageal echocardiography has provided visual evidence that clamp removal after CABG releases a shower of embolic particles. The quantity of released emboli is a function of the severity of aortic atheromatosis and is strongly correlated to neurocognitive deterioration.

Though incidence is less, aortic aneurysm repair likewise elevates the number of embolic particles. Repair is usually accomplished in an open manner, but minimally invasive approaches are in development.

There are a number of known devices for removing clot or filtering particles from blood. U.S. Pat. No. 4,723,549 to Wholey et al. discloses a device for dilating occluded blood vessels that includes a collapsible filter device positioned between a dilating balloon and the distal end of the catheter. The filter comprises a plurality of resilient ribs secured to the catheter that extend axially toward the dilating balloon. Filter material is secured to the ribs. The filter deploys as a filter balloon is inflated to form a cup-shaped trap. The filter does not seal around the interior vessel wall. Thus, particles can pass between the filter and the vessel wall. The device also presents a large profile during positioning and is difficult to construct.

U.S. Pat. No. 4,873,978 to Ginsburg discloses a vascular catheter that includes a strainer device at its distal end. The device is inserted into a vessel downstream from the treatment site and advanced to a proximal downstream location. The filter is contained in a sheath when closed. When pushed from the sheath, the filter deploys such that its mouth spans the lumen of the vessel. Deployment is by expansion of resilient tines to which the strainer material is attached. The filter does not seal around the interior vessel wall. Thus particles can pass between the filter and the vessel wall. The position of the mouth relative to the sheath is clinically limiting.

U.S. Pat. No. 5,695,519 to Summers et al. discloses a removable intravascular filter on a hollow guide wire for entrapping and retaining emboli. The filter is deployable by manipulation of an actuating wire that extends from the filter into and through the hollow tube and out the proximal end. During positioning within a vessel, the filter material is not fully constrained so that, as the device is positioned through and past a clot, the filter material can snag clot material creating freely floating emboli. It is unclear if the actuating wire can close the filter, but may, in fact, exert a pull force on the rim of the filter that can tear the wire from the rim. Device application is limited by the diameter of the tube needed to contain the actuating wire.

U.S. Pat. No. 5,814,046 to Daniel et al. discloses an emboli capture device on a guide wire. The filter material is coupled to a distal portion of the guide wire and is expanded across the lumen of a vessel by a fluid activated expandable member in communication with a lumen running the length of the guide wire. During positioning, as the device is passed through and beyond the clot, filter material may interact with the clot to produce emboli. It is believed that the device may also be difficult to manufacture.

PCT Publication No. WO 98/33443 discloses a removable vascular filter wherein the filter material is fixed to cables or spines mounted to a central guide wire. A movable core or fibers inside the guide wire can be utilized to transition the cables or spines from approximately parallel to the guide wire to approximately perpendicular the guide wire. The filter does not seal around the interior vessel wall. Thus, particles can pass between the filter and the vessel wall. This umbrella-type device is shallow when deployed so that, as it is being closed for removal, particles can escape. The frame is such that the introduction profile presents a risk of generating emboli as the device is passed through and beyond the stenosis.

U.S. Pat. No. 5,769,816 to Barbut et al. discloses a device for filtering blood within a blood vessel. The device is delivered through a cannula and consists generally of a cone-shaped mesh with apex attached to a central support and open edge attached to an inflation seal that can be deflated or inflated. The seal is deflated during delivery and when delivery is complete, it is inflated to seal the filter around the lumen of the vessel. The device is suitable for large vessels such as the aorta, but is difficult to scale for smaller vessels such as the carotid or the coronary arteries.

U.S. Pat. No. 5,549,626 to Miller et al. discloses a coaxial filter device for removing particles from arteries and veins consisting of an outer catheter that can be inserted into a blood vessel and an inner catheter with a filter at its distal end. The filter is a radially expandable receptacle made of an elastic mesh structure of spring wires or plastic monofilaments. When pushed from the distal end of the catheter, the filter deploys across the vessel lumen. A syringe attached to the proximal end of the inner catheter aspirates particles entrapped in the filter. However, it is possible that some particles remain in the filter after aspiration such that, when the filter is retracted into the outer catheter, particles not aspirated are released.

Permanent filters for the vena cava are well-established clinical devices. These open filters capture large emboli passing from a surgical site to the lungs. U.S. Pat. No. 3,952,747 to Kimmel et al. discloses the Kimray-Greenfield filter. It is a permanent filter typically placed in the vena cava and consists of a plurality of convergent legs in a generally conical array that are joined at their convergent ends to an apical hub. Each leg has a hook at its end to impale the interior wall of the vena cava. U.S. Pat. Nos. 4,425,908 to Simon; 4,688,553 to Metals; and 4,727,873 to Mobin-Uddin et al. are also illustrative of such devices.

U.S. Pat. Nos. 5,669,933 and 5,836,968 to Simon et al. are illustrative of removable blood clot filters suitable for the venous system, specifically the vena cava.

It is, therefore, an object of the present invention to overcome the above problems and others by providing a guide wire positionable device which can be easily inserted and removed from a body canal, such as a blood vessel, which can be readily deployed and retracted in the body canal, which avoids injury to the body canal when deployed and which removes solid objects, such as emboli, from the body canals when deployed. Still other objects will become apparent to those of ordinary skill in the art upon reading and understanding the following detailed description.

SUMMARY OF THE INVENTION

Accordingly, I have invented a filter apparatus for removing a solid object from a body canal. The filter apparatus includes a sheath and a sack having a mouth and a closed bottom opposite the mouth. A guide wire is received in the sheath for relative longitudinal movement therebetween. The guide wire projects through the mouth of the sack and the closed bottom of the sack. The closed bottom of the sack is connected to the projection of the guide wire therethrough. A wire frame is connected between the guide wire and the mouth of the sack for urging the mouth of the sack open around the guide wire. The wire frame is moveable via the guide wire between outside the sheath where the mouth of the sack is biased open by the wire frame and inside the sheath where the mouth of the sack is closed against the bias of the wire frame by interaction between the wire frame and the inside of the sheath, and vice versa.

The wire frame can include at least a partial loop connected to the mouth of the sack and a plurality of control arms connected between the at least partial loop and the guide wire. When the wire frame is positioned outside the sheath, the at least partial loop extends transverse, preferably perpendicular, to the longitudinal axis of the guide wire and the inside radius of the at least partial loop faces the guide wire.

The at least partial loop is continuous between the plurality of control arms or is a plurality of arcuate segments, with each arcuate segment extending from one control arm and terminating at an end touching or in spaced relation with an end of another arcuate segment extending from another control arm.

Each control arm can be connected to the guide wire at a junction position on a side of the mouth of the sack opposite the closed bottom of the sack. When the wire frame is positioned outside the sheath, the plurality of control arms diverge from the junction to the at least partial loop which extends transverse to the longitudinal axis of the guide wire with the inside radius of the at least partial loop facing the guide wire. When the wire frame is received inside the sheath, the plurality of control arms and the at least partial loop form an elongated loop having a longitudinal axis substantially parallel to the longitudinal axis of the guide wire.

The wire frame can include a plurality of frame parts positioned around the guide wire. Each frame part has a partial loop connected to the mouth of the sack and at least one control arm connected between the at least partial loop and the guide wire. When each frame part is positioned outside the sheath, the at least one control arm thereof diverges from the guide wire to the at least partial loop which extends transverse to the longitudinal axis of the guide wire with the inside radius of the at least partial loop facing the guide wire. When each frame part is received inside the sheath, the at least one control arm thereof and the at least partial loop extends substantially parallel to the longitudinal axis of the guide wire. The wire frame can include a pair of frame parts positioned in mirror image relation. At least one of the wire frame, the sack, the guide wire and the sheath can include a biocompatible, radiopaque material.

I have also invented a vascular filter for capturing and removing emboli. The filter includes a sack having a mouth and a closed bottom opposite the mouth. A guide wire is received through the mouth of the sack and projected through the closed bottom of the sack. The closed bottom of the sack is connected to the projection of the guide wire therethrough. A collapsible frame is connected between the guide wire and the mouth of the sack. The collapsible frame biases the mouth of the sack open around the guide wire. A tube slidably receives the guide wire coaxially therein. The collapsible frame is moveable via the guide wire between outside the tube where the mouth of the sack is biased open and inside the tube where the mouth of the sack is closed, and vice versa.

The collapsible frame biases a mouth of the sack open when the collapsible frame is outside the tube. The collapsible frame closes the mouth of the sack in response to interaction between the collapsible frame and the inside of the tube when the collapsible frame is received in the tube.

The collapsible frame has at least a partial loop connected to the mouth of the sack and a plurality of control arms connected between the at least partial loop and the guide wire. The at least partial loop extends transverse to the longitudinal axis of the guide wire with an inside radius of the at least partial loop facing the guide wire.

The collapsible frame can include a plurality of collapsible frame parts positioned around the guide wire. Each collapsible frame part has a partial loop connected to the mouth of the sack and a plurality of control arms connected between the at least partial loop and the guide wire. Each partial loop extends transverse to the longitudinal axis of the guide wire with an inside surface of each partial loop facing the guide wire. The collapsible frame can include a pair of collapsible frame parts positioned in mirror image relation. A pliable tip can be connected to an end of the guide wire adjacent the closed bottom of the sack.

Lastly, I have invented a device for removing a solid object from a blood vessel. The device includes a tube and a collapsible basket having a mouth, a bottom and a plurality of control arms connected to the mouth and extending away from the bottom. A guide wire is received in the tube and projected through the mouth and the bottom. The ends of the plurality of control arms opposite the mouth are connected to the guide wire. The bottom of the collapsible basket is connected to the projection of the guide wire therethrough.

The mouth of the collapsible basket is moveable via the guide wire between outside the tube where the mouth of the collapsible basket is open and inside the tube where the mouth of the collapsible basket is closed, and vice versa.

The collapsible basket includes a flexible sack and a wire frame. The flexible sack includes the mouth and the bottom. The wire frame includes the plurality of control arms connected to at least a partial loop which is connected to the mouth of the sack and which extends transverse to the longitudinal axis of the guide wire when the frame is positioned outside the tube. The inside radius of the at least partial loop faces the guide wire. The wire frame and sack are moveable via the guide wire between outside the tube where the control arms diverge from the guide wire to the at least partial loop whereby the mouth of the sack is open and inside the tube where the control arms and the at least partial loop are adjacent the guide wire whereby the mouth of the sack is closed, and vice versa.

The wire frame is preferably formed from a shaped-memory-effect material. The wire frame is configured to be firm and pliable so that interactions between the wire frame and the intima of a blood vessel avoids damage to the blood vessel. The sack material can be porous or a non-porous material.

DETAILED DESCRIPTION OF THE PREFERRED EMBODIMENTS

Figure 1:
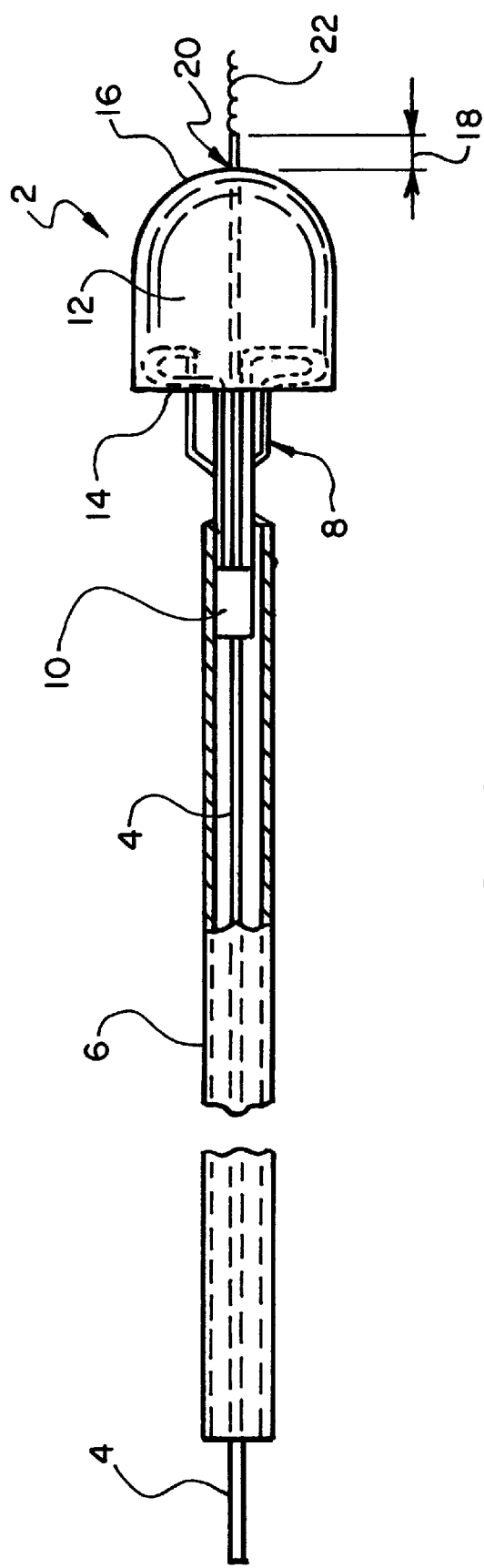
FIG. 1 is a schematic view, partially cut away, of an interventional device in accordance with the present invention including a sack connected to a wire frame which is connected to a guide wire received in a tubular sheath.

With reference to FIG. 1, a surgical device 2 for capturing and removing solid particles from a body cavity, such as a blood vessel, includes a guide wire 4 received in a tube or tubular sheath 6. A wire frame 8 is connected to guide wire 4 via a junction 10. A sack 12 has a open end or mouth 14 connected to an end of wire frame 8 opposite junction 10 and a closed end or bottom 16 opposite mouth 14. Guide wire 4 projects through mouth 14 and bottom 16 and terminates at a distal end a distance 18 from bottom 16 of sack 12. Preferably, bottom 16 of sack 12 has a hemispherical shape and guide wire 4 extends though an apex 20 of the hemispherically-shaped bottom 16. Bottom 16 of sack 12 is connected to the projection of guide wire 4 therethrough.

A pliable tip 22 is preferably connected to the distal end of guide wire 4. Pliable tip 22 is formed from a biocompatible material having a spring memory. Preferably, the biocompatible material forming pliable tip 22 is wound into a coil with one end of pliable tip 22 attached to the distal end of the guide wire 4 and with the other end of pliable tip 22 extending away from guide wire 4. Pliable tip 22 enables the distal end of guide wire 4 and tubular sheath 6, with wire frame 8 received therein in a manner described hereinafter, to be readily advanced in a blood vessel.

Tubular sheath 6 is preferably made from Teflon, however, tubular sheath 6 can be made from other flexible, biocompatible materials, such as polyethylene, nylon or polyimides that permit relative longitudinal movement between guide wire 4 and tubular sheath 6. To promote relative longitudinal movement therebetween, the inside surface of tubular sheath 6 and/or guide wire 4 can be coated with a tough, flexible, lubricious coating, such as Teflon or a hydrophilic film. Moreover, the inside surface of tubular sheath 6 and/or guide wire 4 can receive a biocompatible lubricant, such as silicon.

Figure 2:
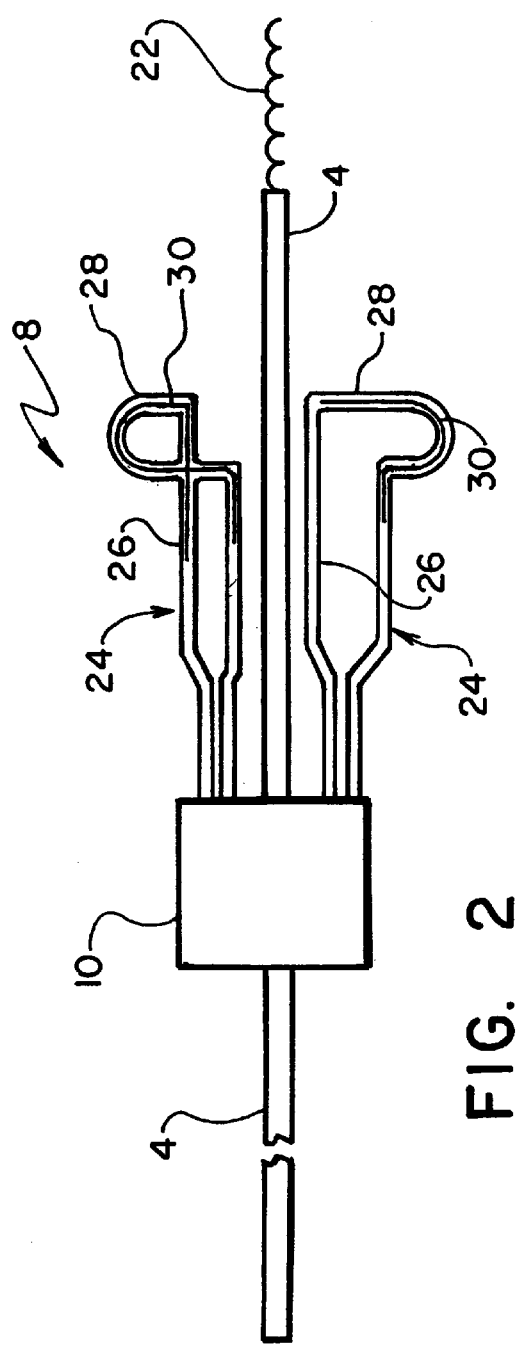
FIG. 2 is a schematic view of the guide wire and wire frame of FIG. 1 with the wire frame in a deployed state.

With reference to FIG. 2, and with continuing reference to FIG. 1, wire frame 8 includes a pair of half frames 24 connected in mirror image relation to guide wire 4 via junction 10. Each half frame 24 has a pair of control arms 26 connected at their proximal ends to guide wire 4 via junction 10. Junction 10 can be a crimp of biocompatible material or a weld that connects half frames 24 to guide wire 4. The distal end of each half frame 24 has a partial loop 28 that extends between control arms 26. Half frames 24 are constructed of a shape-memory-effect alloy, such as Nitinol, in its super-elastic state. The shape-memory-effect alloy enables each half frame 24 to be "trained" or formed so that in a relaxed, undeformed state control arms 26 diverge between junction 10 and partial loop 28 and partial loop 28 extends transverse, preferably perpendicular, to the longitudinal axis of guide wire 4, with an inside radius of each partial loop 28 facing guide wire 4.

In another embodiment, each half frame 24 includes an arcuate section (not shown) connected to the distal end of each control arm 26. The arcuate sections extend from their respective control arms 26 and terminate with their ends touching or in spaced relation forming a gap therebetween. The arcuate sections can be formed by separating each partial loop 28 intermediate control arms 26, as shown by the dashed lines in FIG. 2. The arcuate sections can be configured to form a partial or complete loop. In yet another embodiment, wire frame 8 can include a complete loop (not shown) connected to the distal ends of the control arms 26.

To enable wire frame 8 to be viewed more clearly under fluoroscopic visualization inside a blood vessel, a wire or thread 30 made from a biocompatible, radiopague material (s) is bonded to one or more partial loops 28, one or more control arms 26 and/or woven into the rim of mouth 14 of sack 12. Alternatively, partial loops 28 and/or control arms 22 are coated with the biocompatible, radiopague material (s). To enable pliable tip 22 to be viewed under fluoroscopic visualization inside a blood vessel, at least the distal end of pliable tip 22 is made from or coated with the biocompatible, radiopague material(s). Examples of biocompatible, radiopague materials) include gold, tungsten and platinum or combinations thereof.

Figure 3:
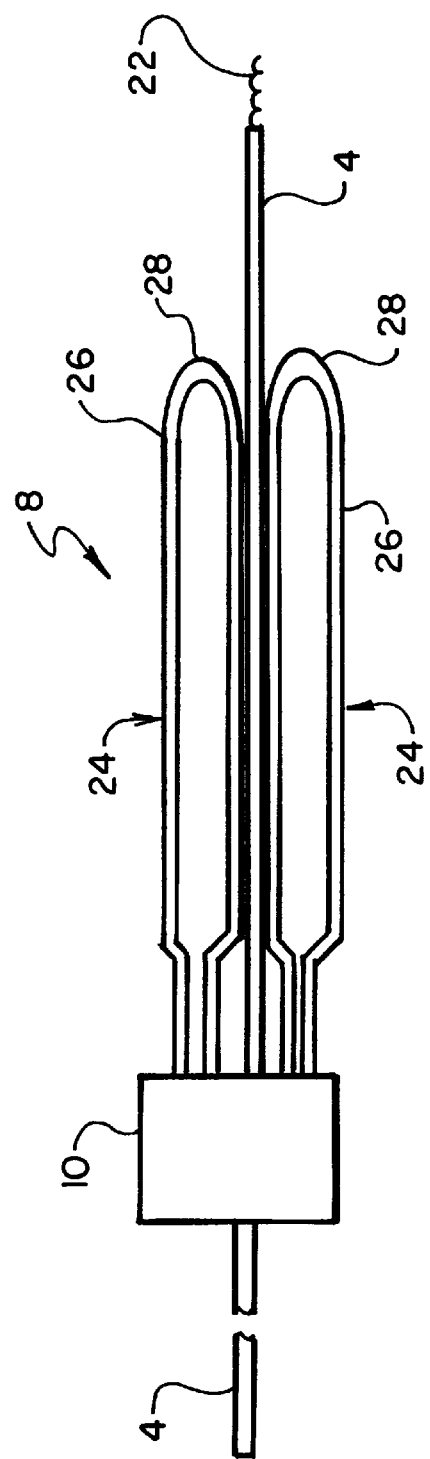
FIG. 3 is a schematic view of the guide wire and wire frame of FIG. 1 with the wire frame in a retracted state.
Figure 4:
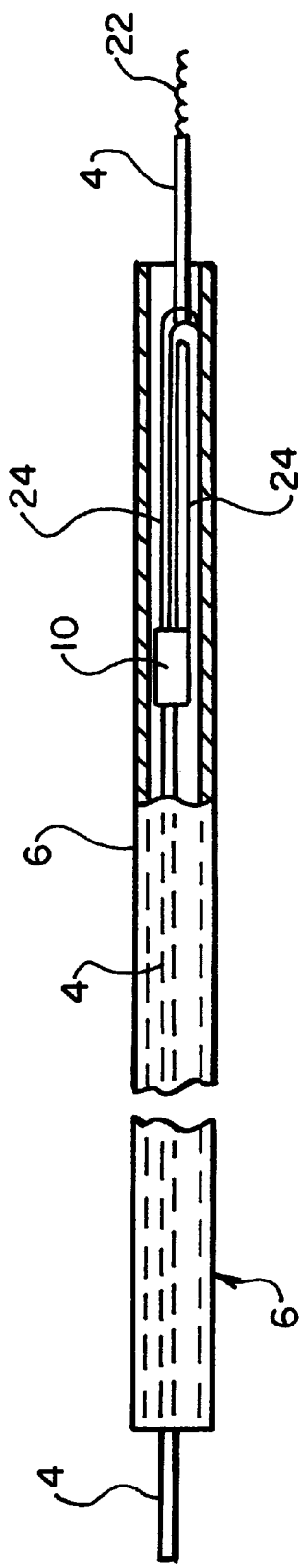
FIG. 4 is a schematic view, partially cut away, of the interventional device of FIG. 1, with the wire frame retracted into the tubular sheath.

Retracting wire frame 8 into tubular sheath 6 causes control arms 26 to interact with tubular sheath 6 whereby control arms 26 and partial loops 28 deform and, more particularly, converge toward guide wire 4 as they are received in tubular sheath 6. As shown in FIGS. 3 and 4, when control arms 26 and partial loops 28 of half frames 24 are received in tubular sheath 6, they are stressed within the elastic limits of the shape-memory-effect alloy to form elongated loops having axes positioned substantially parallel to the longitudinal axis of guide wire 4. The super-elastic property of the shape-memory-effect alloy enables half frames 24 to return to the relaxed, undeformed shape shown in FIG. 2 when they are deployed from tubular sheath 6.

Sack 12 is formed of a biocompatible material having sufficient strength to withstand forces associated with deployment in blood vessels and forces associated with ensnaring/retaining particles within sack 12. The material may be either non-porous or porous. Sack 12 made of non-porous material occludes blood flow in blood vessels. Sack 12 made of porous material allows blood flow in blood vessels, but permits particles of smaller diameter than the pores of sack 12 to escape therethrough. Preferably, sack 12 is formed from of a polymeric material, such as polyurethane, which is either porous or non-porous. Sack 12 can also be made radiopaque through the addition thereto of barium sulfate or bismuth sulfate. Sack 12 can also be made of other biocompatible materials, such as woven polyester fabrics.

A rim of mouth 14 of sack 12 surrounds and is bonded to half frames 24 to secure sack 12 to wire frame 8. Similarly, bottom 16 of sack 12 is bonded to the projection of guide wire 4 therethrough to secure sack 12 to guide wire 4. Chemicals and/or heat can be utilized to bond sack 12 to guide wire 4 and wire frame 8. Preferably, sack 12 is bonded between half frames 24 and guide wire 4 so that no gaps exist between sack 12 and guide wire 4 and sack 12 and wire frame 8.

The size of the blood vessel lumen receiving wire frame 8 establishes the dimensions of wire frame 8 in its deployed state that can be utilized to capture particulate or remove solid material. Specifically, the dimensions of wire frame 8 in its deployed state are selected to form a seal between the mouth 14 of sack 12 and the intima of the vessel. Preferably, wire frame 8 is configured to be firm and pliable so that interaction between the wire frame 8 and the intima of the blood vessel avoids trauma to the blood vessel. In an exemplary embodiment, the control arms 26 and the partial loops 28 of wire frame 8 have diameters between 0.003 to 0.010 inch, guide wire 4 has a diameter between 0.010 to 0.035 inch and tubular sheath 6 has an outside diameter between 0.025 to 0.130 inch.

The lengths of tubular sheath 6 and guide wire 4 are selected based on the position of a vascular access for inserting surgical device 2 in the lumen relative to the position in the lumen of the solid material or the blood vessel to be protected from movement of particulate.

Figure 5:
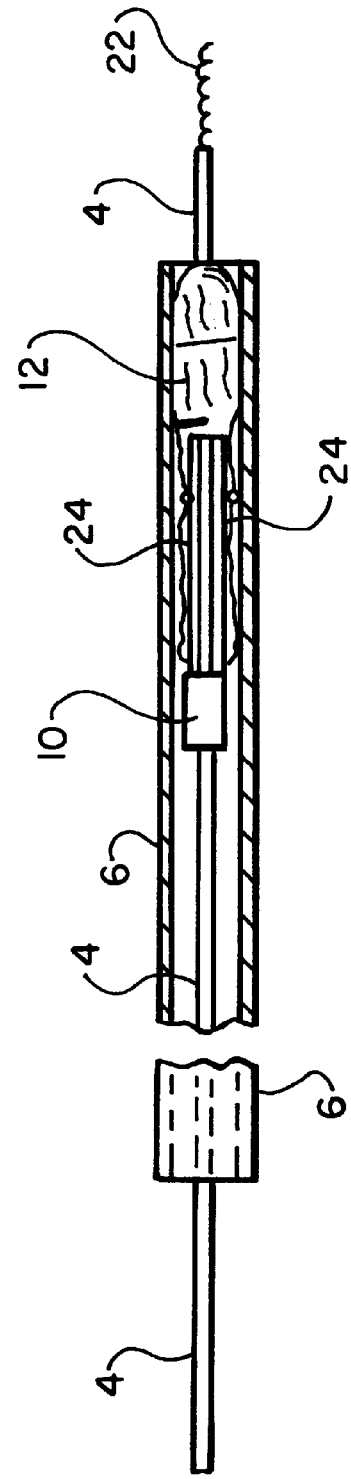
FIG. 5 is a schematic view, partially cut away, of the interventional device of FIG. 4 including the sack attached to the wire frame and retracted into the tubular sheath.

Surgical device 2 can be used in several ways depending on its exact configuration and the area of the cardiovascular system involved. Use of surgical device 2 to capture emboli shed during angioplasty and stent placement in the carotid artery will now be described with reference to FIGS. 1, 5 and 6.

Starting with wire frame 8 and sack 12 retracted into tubular sheath 6 and with at least pliable tip 22 extending from tubular sheath 6, pliable tip 22 is inserted percutaneously into a patient, followed by the remainder of guide wire 4 and tubular sheath 6. Under fluoroscopic visualization, tubular sheath 6 is manipulated to advance pliable tip 22 across a stenosis in the carotid artery. Tubular sheath 6 is then positioned so that when deployed, wire frame 8 and sack 12 are positioned downstream of the stenosis in the carotid artery to capture and retain emboli particulate.

To deploy wire frame 8 and sack 12, a portion of guide wire 4 outside the patient's body is held steady and a portion of tubular sheath 6 outside the patient's body is pulled away from wire frame 8 and sack 12. Thereafter, tubular sheath 6 is removed from guide wire 4 thereby enabling other "over-the-wire" components used during the procedure to be received on guide wire 4.

Figure 6:
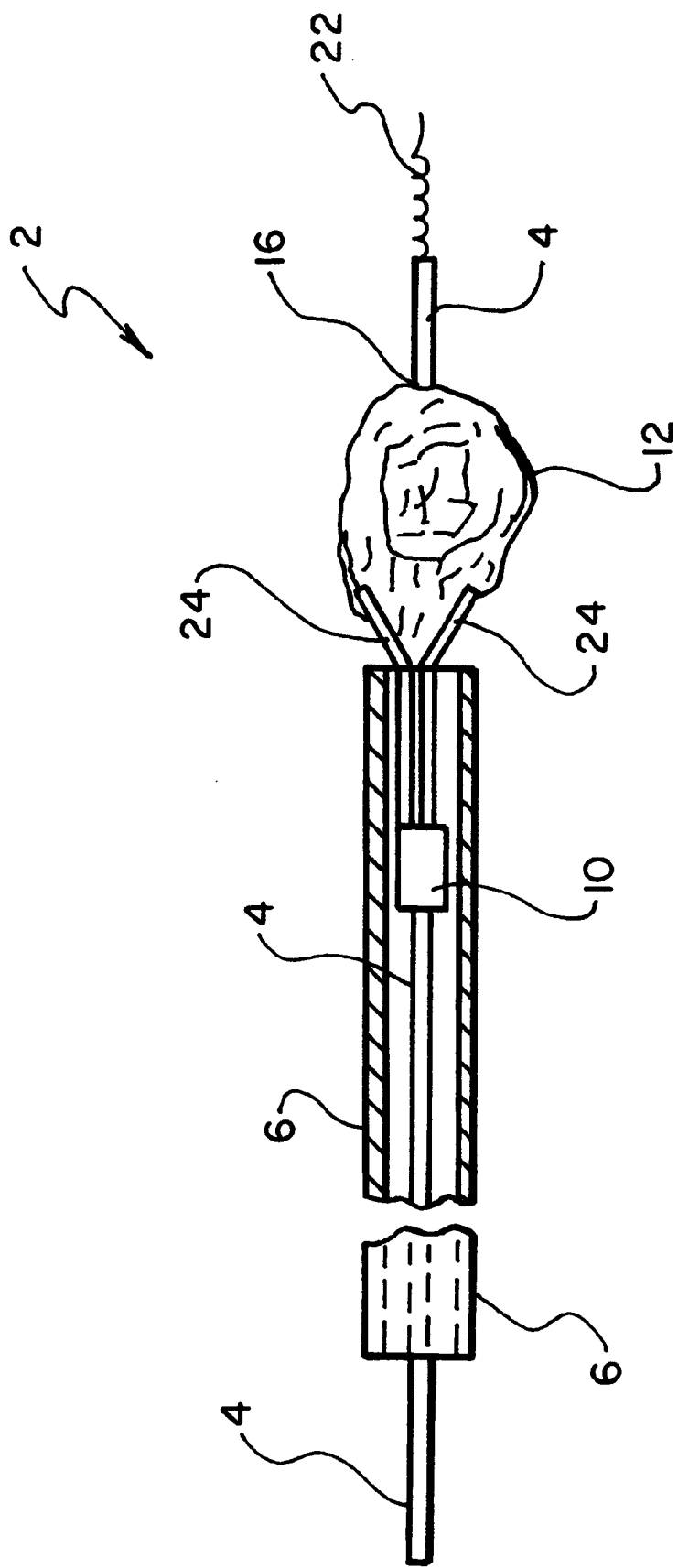
FIG. 6 is a schematic view, partially cut away, of the interventional device shown in FIG. 1 with an object received in the sack, and with the wire frame and the sack partially retracted into the tubular sheath.

After the stenosis has been reduced and the other "over-the-wire" components removed from guide wire 4, tubular sheath 6 is positioned over guide wire 4 and advanced toward wire frame 8 and sack 12. Tubular sheath 6 positioned over guide wire 4 can have a larger diameter than tubular sheath 6 removed from guide wire 4. Wire frame 8 is retracted into tubular sheath 6 by holding steady the portion of guide wire 4 outside the patient's body and by urging the portion of tubular sheath 6 outside the patient's body toward wire frame 8 and sack 12 until wire frame 8 is received in tubular sheath 6. As shown in FIG. 6, particulate captured in sack 12, may permit only partial retraction of sack 12 into tubular sheath 6. However, the particulate captured in sack 12 cannot empty or escape into the carotid artery. Thereafter, tubular sheath 6, wire frame 8, sack 12 and the particulate captured in sack 12 are withdrawn from the patient.

As can be seen, surgical device 2 enables emboli shed during angioplasty and stenting procedures to be safely captured and removed. Its design facilitates scaling for use in various diameter vessels. The shape-memory-effect alloy permits wire frame 8 to form a seal with the intima of a blood vessel while avoiding trauma to the blood vessel. Pliable tip 22 and/or the extension of the distal end of guide wire 4 and the distance 18 beyond bottom 16 of sack 12 permits manipulation of surgical device 2 through tortuous vascular configurations. Guide wire 4 enables delivery of other devices to the angioplasty and stent site. Sack 12 connected to wire frame 8 coacts to form a basket that can be manipulated to a position outside tubular sheath 6 where the mouth of the basket is open and a position inside tubular sheath 6 where the mouth of the basket is closed, and vice versa. The material used to construct sack 12 can be porous or non-porous. When sack 12 is made of a porous material, it acts as a filter that allows blood to flow and captures particles of a size greater than the pores. When sack 12 is made of a non-porous material, it occludes blood flow and movement of solid particles thereby. A suction device can then be used to remove particles trapped by sack 12 of non-porous material.

The invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

I claim:

1. A filter apparatus for removing a solid object from a body canal, the filter apparatus comprising:
   a sheath;
   a sack having a mouth and a closed bottom opposite the mouth;
   a guide wire received in the sheath for relative longitudinal movement therebetween, the guide wire projecting through the mouth of the sack and the closed bottom of the sack, the closed bottom of the sack connected to the projection of the guide wire therethrough; and
   a wire frame connected between the guide wire and the mouth of the sack for urging the mouth of the sack open around the guide wire, wherein the wire frame is movable via the guide wire between outside the sheath where the mouth of the sack is biased open by the wire frame and inside the sheath where the mouth of the sack is closed against the bias of the wire frame by interaction of the wire frame with the inside of the sheath, and vice versa.

2. The filter apparatus as set forth in claim 1, wherein the wire frame includes at least a partial loop connected to the mouth of the sack and a plurality of control arms connected between the at least partial loop and the guide wire.

3. The filter apparatus as set forth in claim 2, wherein when the wire frame is positioned outside the sheath, the at least partial loop extends transverse to the longitudinal axis of the guide wire and the inside radius of the at least partial loop faces the guide wire.

4. The filter apparatus as set forth in claim 2, wherein the at least partial loop is one of:
(i) continuous between the plurality of control arms; and
(ii) a plurality of arcuate segments, each arcuate segment extending from one control arm and terminating at an end touching or in spaced relation with an end of another arcuate segment extending from another control arm.

5. The filter apparatus as set forth in claim 2, wherein:
each control arm is connected to the guide wire at a junction positioned on a side of the mouth of the sack opposite the closed bottom of the sack;
when the wire frame is positioned outside the sheath, the plurality of control arms diverge from the junction to the at least partial loop which extends transverse to the longitudinal axis of the guide wire with the inside radius of the at least partial loop facing the guide wire; and
when the wire frame is received inside the sheath, the plurality of control arms and the at least partial loop forms an elongated loop having a longitudinal axis substantially parallel to the longitudinal axis of the guide wire.

6. The filter apparatus as set forth in claim 1, wherein:
the wire frame includes a plurality of frame parts positioned around the guide wire;
each frame part has a partial loop connected to the mouth of the sack and at least one control arm connected between the at least partial loop and the guide wire;
when each frame part is positioned outside the sheath, the at least one control arm thereof diverges from the guide wire to the at least partial loop which extends transverse to the longitudinal axis of the guide wire with the inside radius of the at least partial loop facing the guide wire; and
when each frame part is received inside the sheath, the at least one control arm thereof and the at least partial loop extend substantially parallel to the longitudinal axis of the guide wire.

7. The filter apparatus as set forth in claim 6, wherein the wire frame includes a pair of the frame parts positioned in mirror image relation.

8. The filter apparatus as set forth in claim 1, wherein at least one of the wire frame, the sack, the guide wire and the sheath includes a biocompatible, radiopaque material.

9. A vascular filter for capturing and removing emboli, the filter comprising:
a sack having a mouth and a closed bottom opposite the mouth;
a guide wire received through the mouth of the sack and projecting through the closed bottom of the sack, the closed bottom of the sack connected to the projection of the guide wire therethrough;
a collapsible frame connected between the guide wire and the mouth of the sack, the collapsible frame biasing the mouth of the sack open around the guide wire; and
a tube which slidably receives the guide wire coaxially therein, wherein the collapsible frame is movable via the guide wire between outside the tube where the mouth of the sack is biased open by the collapsible frame and inside the tube where the mouth of the sack is closed, and vice versa.

10. The filter as set forth in claim 9, wherein:
the collapsible frame biases the mouth of the sack open when the collapsible frame is outside the tube; and
the collapsible frame closes the mouth of the sack in response to interaction between the collapsible frame and the inside of the tube when the collapsible frame is received in the tube.

11. The filter as set forth in claim 9, wherein the collapsible frame has at least a partial loop connected to the mouth of the sack and a plurality of control arms connected between the at least partial loop and the guide wire.

12. The filter as set forth in claim 11, wherein the at least partial loop extends transverse to the longitudinal axis of the guide wire with an inside radius of the at least partial loop facing the guide wire.

13. The filter as set forth in claim 9, wherein the collapsible frame includes a plurality of collapsible frame parts positioned around the guide wire, each collapsible frame part having a partial loop connected to the mouth of the sack and a plurality of control arms connected between the at least partial loop and the guide wire, each partial loop extending transverse to the longitudinal axis of the guide wire with an inside radius of each partial loop facing the guide wire.

14. The filter as set forth in claim 13, wherein the collapsible frame includes a pair of the collapsible frame parts positioned in mirror image relation.

15. The filter as set forth in claim 9, further including a pliable tip connected to an end of the guide wire adjacent the closed bottom of the sack.

16. A device for removing a solid object from a blood vessel, the device comprising:
a tube;
a collapsible basket having a mouth, a bottom and a plurality of control arms connected to the mouth and extending away from the bottom; and
a guide wire received in the tube and projecting through the mouth and the bottom, the ends of the plurality of control arms opposite the mouth connected to the guide wire, the bottom of the collapsible basket connected to the projection of the guide wire therethrough, wherein the mouth of the collapsible basket is moveable via the guide wire between outside the tube where the mouth of the collapsible basket is open and inside the tube where the mouth of the collapsible basket is closed, and vice versa.

17. The device as set forth in claim 16, wherein the collapsible basket includes:
a flexible sack having the mouth and the bottom; and
a wire frame having the plurality of the control arms connected to at least a partial loop which is connected to the mouth of the sack and which extends transverse to the longitudinal axis of the guide wire when the wire frame is positioned outside the tube, the inside radius of the at least partial loop facing the guide wire.

18. The device as set forth in claim 17, wherein the wire frame and sack are moveable via the guide wire between outside the tube where the control arms diverge from the guide wire to the at least partial loop whereby the mouth of the sack is open and inside the tube where the control arms and the at least partial loop are adjacent the guide wire whereby the mouth of the sack is closed, and vice versa.

19. The device as set forth in claim 16, wherein:

the wire frame is formed from a shape-memory-effect material; and the wire frame is configured to be firm and pliable so that interaction between the wire frame and the intima of a blood vessel avoids damage to the blood vessel.

20. The device as set forth in claim 17, wherein the sack is made from a porous or a non-porous material.

* * * * *